United States Patent [19]
Griffiths

[11] Patent Number: 5,344,428
[45] Date of Patent: Sep. 6, 1994

[54] MINIATURE SURGICAL INSTRUMENT

[75] Inventor: Jerry R. Griffiths, Pembroke, Mass.

[73] Assignee: Auburn International, Inc., Danvers, Mass.

[21] Appl. No.: 82,559

[22] Filed: Jun. 28, 1993

Related U.S. Application Data

[63] Continuation-in-part of Ser. No. 43,185, Apr. 6, 1993, and a continuation-in-part of Ser. No. 26,861, Mar. 5, 1993.

[51] Int. Cl.$^5$ .............................................. A61B 17/28
[52] U.S. Cl. .................................... 606/205; 128/751; 606/170
[58] Field of Search ............................... 606/205–211, 606/51, 52, 83, 170, 174; 128/750–755; 604/22

[56] References Cited

U.S. PATENT DOCUMENTS

| | | | |
|---|---|---|---|
| 4,674,501 | 6/1987 | Greenberg | 606/205 |
| 5,176,702 | 1/1993 | Bales et al. | 606/205 |

Primary Examiner—Peter A. Aschenbrenner
Assistant Examiner—William Lewis
Attorney, Agent, or Firm—Jerry Cohen; Edwin H. Paul

[57] ABSTRACT

A miniature surgical instrument (10) comprises a handle (12), shaft assembly (26) with an actuating linkage (L1, L2) movable freely therein and a distal working tip (30) with a shaft rotation sub-assembly (22, 24, 34) including multiple spring-stop pairs (40, 38) arranged in an annulus (44) around the shaft to receive cleansing water via an injection port (52) and/or through the handle and to pass it to the interior of the shaft via a port (12C) or past a seal (56) for flow of water in the shaft around the linkage and exiting in the tip vicinity to clear away surgical debris, the arranging allowing independent operation of the linkage, a lock (14) for the linkage and the tip rotation means. The arrangement prevents or minimizes debris accumulation in the first instance through its avoidance of a pressure differential from an insufflated body cavity to ambient air via the instrument.

1 Claim, 2 Drawing Sheets

MINIATURE SURGICAL INSTRUMENT

CROSS REFERENCE TO RELATED APPLICATIONS

This application is a continuation-in-part of my co-pending prior U.S. application, Ser. No. 08/043,185, filed Apr. 6, 1993 and U.S. application, Ser. No. 08/026,861, filed Mar. 5, 1993.

FIELD OF THE INVENTION

The present invention relates to various types of miniature surgical instruments, such as are used e.g. in endoscopic surgery, including e.g. as to endoscopy and other fields, forceps, graspers, needle holders, scissors and punches differentiated by their working tip designs but using a common handle and tubular shafts, varying in length and/or diameter.

BACKGROUND OF THE INVENTION

It is the object of the invention to provide a practical means for easily setting each of several different rotational orientations of the tip of such instruments yet reliably holding each such setting.

It is a further object of the invention to provide such an instrument with a lockable actuator which can be locked or unlocked.

It is a further object of the invention to provide enhanced cooperative benefit of rotation and locking.

It is a further object of the invention to provide a system for cleansing liquid coatings and solid debris from an instrument and for prevention or minimizing such debris and that meets one or more of the preceding criteria.

It is a further object of the invention to provide for ease of cleansing at scattered locations in a medical services setting.

SUMMARY OF THE INVENTION

Reference is made to my previous applications for a summary description of instruments providing tip locking within its range of tip positions (e.g. jaw opening and closing and in between) and for rotation of the tip to each of a range of rotation settings. The latter feature includes an annulus for using annularly arranged, spring loaded, locking balls which seat into notches of a rotatable member. Cleansing of debris is effected by forcing water or other cleansing liquid or gas through the instrument itself and more particularly through the said annulus and from it to the elongated tubular shaft that contains part of a linkage that extends from the instrument handle to its working tip. The water or other fluid forces debris down the shaft and out through the open spaces at the tip. The water can be forced into the annulus via a syringe or hose or via an enclosure of the instrument end at or near the handle as described in my said application Ser. No. 08/026,861, filed Mar. 5, 1993.

Other objects, features and advantages will be apparent from the following detailed description of preferred embodiments taken in conjunction with the accompanying drawings in which:

DETAILED DESCRIPTION OF PREFERRED EMBODIMENTS

Figure 1:
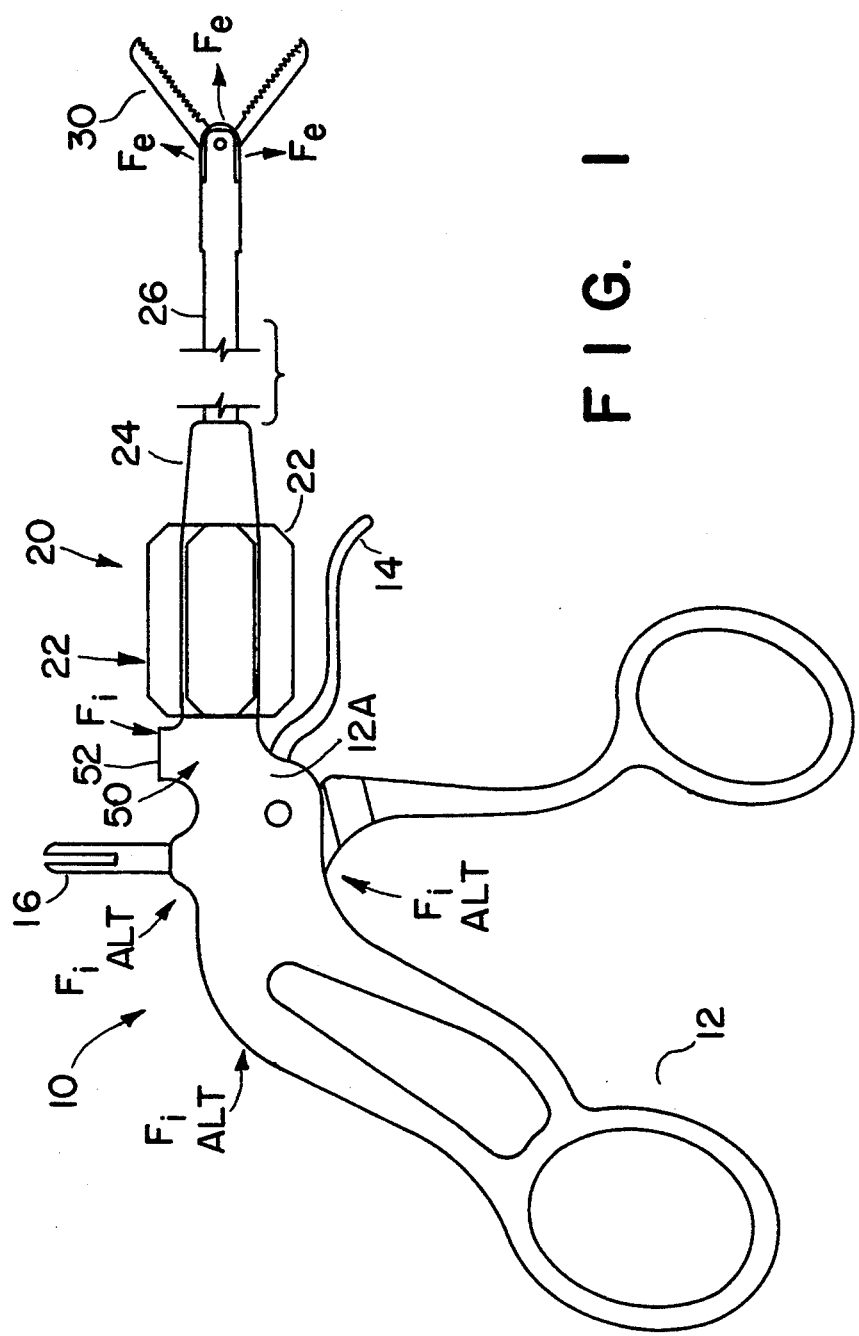
FIG. 1 is a side view of a preferred embodiment of a surgical instrument with rotation.
Figure 2:
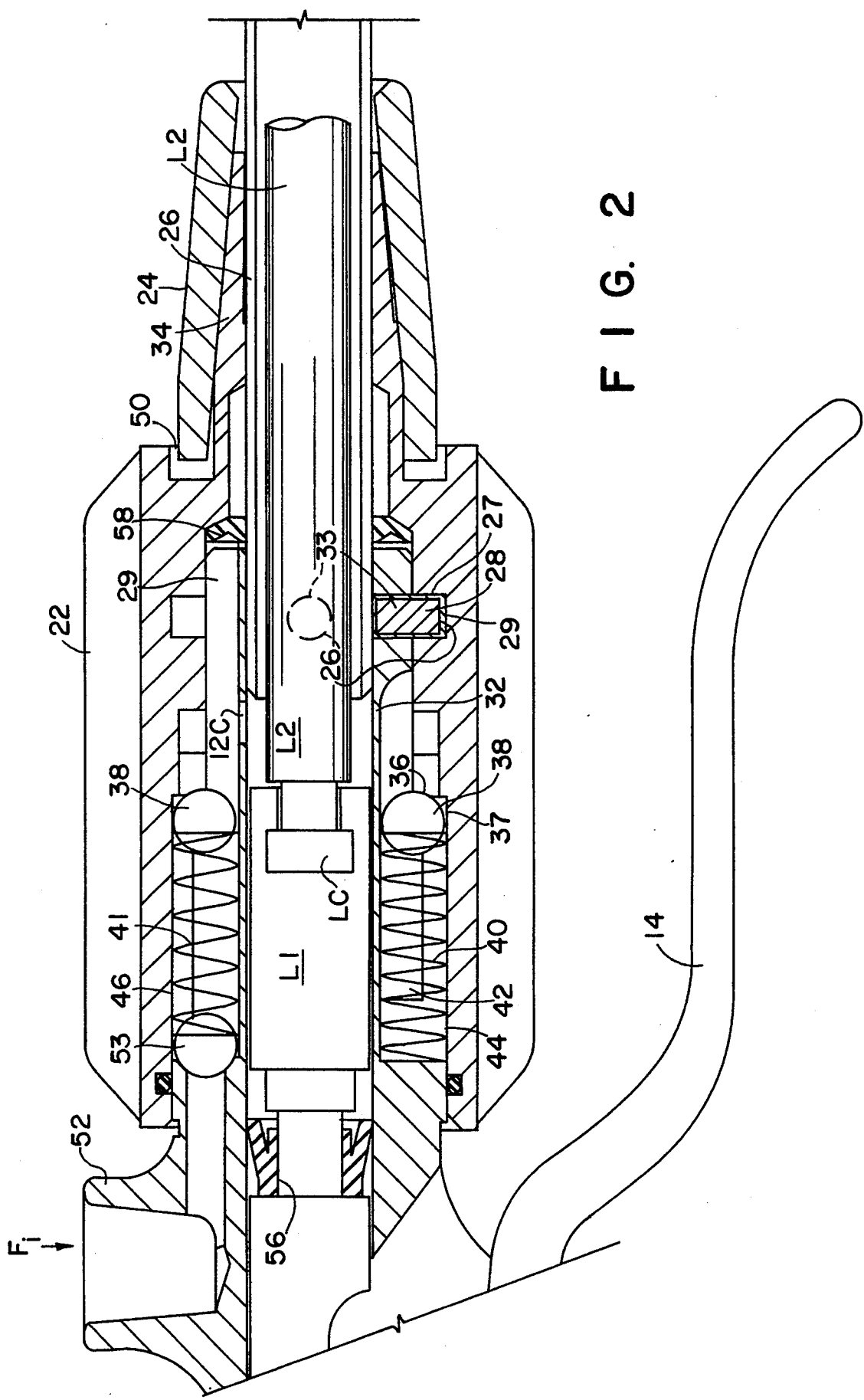
FIG. 2 is a sectioned expanded view of its rotational sub-assembly portion with cleansing features clearly shown.

FIGS. 1-2 show a micro-surgical tool 10 with a scissors handle 12 (with a nose section 12A), lock 14, electrode 16 and a rotatable mechanism 20, the latter including a rotatable knob 22, end cap 24, rotatable tubular shaft 26 secured linearly with knob 22 by retaining pins 28 passing through holes 33 of a tubular extension 32 of nose section 12A and a groove 27 of the knob. An extension 34 of knob 22 grasps tubular shaft 26 and end cap 24 fits over that extension. Rotation of the knob rotates the tubular shaft. A working tip 30 of, e.g., puncher, grasper, cutter or other form is mounted at the distal (from the handle) end of tubular shaft 26 and is rotatable therewith. Cleansing fluid can be injected as indicated at arrow Fi and/or FiALT and exit at the tip as indicated by arrows Fe.

As indicated in FIGS. 1-2, actuating linkage for the tip comprises links L1 and L2 and an interlink connection LC allowing relative rotation. Link L2 passes through the tubular shaft to the tip. Link L1 extends to the handle for operation thereby. The linkage transmits linear actuating motions from the handle to the tip, but allows rotation of the tubular shaft 26 and the tip relative to the plane of the handle. The link L1 can be locked to therefore lock linear activation movement and hence lock the tip in a closed or open or intermediate position, all as described in my said application, Ser. No. 08/043,185, filed Apr. 6, 1993. The knob 22 can have a fluted, knurled or other surface appropriate for ease of one or two finger rotation by the surgeon-user to set the tip 30 at different rotational orientations. The finger(s) doing the rotation can be on the same hand that grasps the handle or from the opposite hand. The instrument can be held steady and in place, e.g. within the surgery site in a body cavity or cannula while making the rotary adjustment of tip orientation.

The handle nose section has an elongated tubular extension 32. The knob 22 terminates in a flexing tube end 34 for grasping the tube 26 and rotating it.

The knob 22 includes a rotational array of notches 36 (preferrably twelve in number; but more or less can be provided). One or more balls 38, each loaded by a spring 40 can fit partially into selected ones of the notches 36, each limited as to linear entrance to the notch by a detent 37. Each spring and ball ride in a groove 42 which is machined within an annulus 44 formed between handle extension 32 and the interior surface 46 of knob 22. The detent and ball are dimensioned so that rotational torque on the knob causes balls to easily ride over the notch—in other words, the rotational force translates into linear force as the ball pushes back against the spring. There is an array of balls 38—two or more of them, distributed in a circular array, preferrably with circumferentially uniform distribution. One of the springs 41 is of a lighter spring force than all the other springs 42 to assure ease of check valve 53 action, but participating with the others in controlling a corresponding circular array of the internal detents of knob 22. This establishes multiple secured rotational positions of the knob (and hence of tubular shaft 26 and tip 30) corresponding to the number of detents.

A circumferential groove 27 in knob 22 houses pins 28 which pass through holes 33 in tube 32 and bear against base of the groove 26S. There is a spherical form 29 of pin ends which sit on surface 26S (FIG. 2) and present minimal frictional resistance to knob rotation.

The knob end 34 has four linear cuts therin to provide it with a spring flexion to grasp tubular shaft 26. An internally tapered end cap 24 is pressed on to extension 34 and so loads the system as to allow integral rotation of the knob and tubular shaft. The end cap fits into an annular forward groove 50 on knob 22. This construction also wards off unauthorized disassembly.

An entrance port 52 is provided for injecting cleansing water or other fluid to the annulus 44 via a syringe or an enclosure with a hose attachment as described, e.g. in my said application Ser. No. 08/026,861, filed Mar. 5, 1993. When such a source of water or other cleansing fluid is used there is a modified cleansing action, i.e. bringing fluid in both through port 52 (and then to port 12C) and also via the handle region generally (i.e. to come toward the region around L1 from the rear). Check valve 53 is pushed aside by water pressure (typically 20–50 psi). An exit port 12C interconnects the annulus to the region of shaft 26 surrounding link L2. Seals 56 and 58 limit the water path to flow through the shaft around link L2 and eventually out through an open shaft end near tip 30, the said pressure being sufficient to remove debris. After such flowing the instrument can be dried and sterilized by conventional methods (e.g., autoclaving). All parts of the instrument are stainless steel or other rust resistant metals (e.g., titanium) except the seals 56, 58 which are elastomers. All such parts can stand up to autoclaving or dry heating exposure. The shape of seal 56 is such that when pressurized fluid comes from the handle region (as mentioned above) the seal itself—of generally annular Vee form—collapses temporarily so long as such pressure is applied and all pressurized fluid (from such source and also via port 52) is eventually expelled at the tip. Upon removal of pressure, seal 56 expands over itself to its sealing (blocking) configuration.

During operation use, a body cavity zone of the operation procedure is pressurized (insufflated) and that pressure is a principal reason for liquids and solids from the operating site entering conventional instruments. Through the construction of the present invention, the above described sealing and the narrow clearances around links L1, L2 an essentially dead air pocket forms throughout the body of the instrument around link L2 (there is no significant air escape, or pressure differential basis, past any of check valve 53 or seals 56, 58). Thus entry of liquids and solids and migration of any that do enter is subsequentially reduced. In cleansing, a complete pick-up of liquid coating of links L1, L2 as well as the internal surface of tubular shaft 26 and all of annulus 44 is achieved.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. In a miniature surgical instrument comprising means defining an essentially pistol form instrument with an actuating handle of scissors form, an elongation tubular shaft with a longitudinal axis, the said shaft mounting at its distal end a working tip of opposed elements, at least one of which is pivotable for moving the elements into and out of working engagement, means defining a linear actuating linkage contained within the shaft and connected to said scissors form handle for linear actuation thereby and linked to the pivotable element(s) to actuate the same through linear movements of the linkage, the improvement comprising:

(a) means for rotating the shaft and locking it in positions to provide different secured rotational positions for the tip and comprising means defining an annulus between parts which are movable relative to each other in a rotational sense, and further comprising in said annulus:
  (i) plural linear spring and stop subassemblies,
  (ii) means defining a rotatable face with notches for receiving the stop members of said subassemblies;
(b) means for admitting cleansing fluid to the annulus, and
(c) passage means leading from the annulus to the shaft to allow passage of cleansing fluid through the shaft around the linkage portion therein and out through an open shaft end near the tip,
(d) means for sealing the instrument against fluid escape through regions other than the tip,
(e) and further comprising seal means to define and limit the said fluid path,
(f) and further comprising an injection port in the handle region and check valve means therefor, and
(g) wherein an additional one of said spring-stop assemblies are provided as a back-up spring to a check valve.

* * * * *

UNITED STATES PATENT AND TRADEMARK OFFICE
CERTIFICATE OF CORRECTION

PATENT NO. : 5,344,428
DATED : September 6, 1994
INVENTOR(S) : Jerry R. Griffiths It is certified that error appears in the above-identified patent and that said Letters Patent is hereby corrected as shown below:

Title page, item [73] Assignee: should read --TNCO., Whitman, Mass.--.

Signed and Sealed this

First Day of August, 1995

Attest:

BRUCE LEHMAN

Attesting Officer

Commissioner of Patents and Trademarks